United States Patent [19]

Duff

[11] Patent Number: 5,234,608
[45] Date of Patent: Aug. 10, 1993

[54] SYSTEMS AND METHODS FOR PROCESSING CELLULAR RICH SUSPENSIONS

[75] Inventor: Daniel H. Duff, Irvine, Calif.

[73] Assignee: Baxter International Inc., Deerfield, Ill.

[21] Appl. No.: 625,943

[22] Filed: Dec. 11, 1990

[51] Int. Cl.⁵ ............... B01D 37/00; B01D 61/00
[52] U.S. Cl. .................... 210/806; 210/97; 210/143; 210/195.2; 210/195.3; 210/257.2; 210/297; 210/321.6; 210/645; 210/651; 210/739; 210/805
[58] Field of Search ............ 210/641, 645, 646, 651, 210/739, 744, 805, 806, 97, 143, 195.2, 195.3, 257.2, 257.1, 295, 297, 321.6, 321.68, 321.82–321.9, 323.1, 324

[56] References Cited

U.S. PATENT DOCUMENTS

| | | |
|---|---|---|
| 3,957,197 | 5/1976 | Sartory et al. |
| 4,191,182 | 3/1980 | Popovich et al. ............ 210/90 |
| 4,322,298 | 3/1982 | Persidsky ............ 210/787 |
| 4,350,594 | 9/1982 | Kawai et al. ............ 210/321.6 |
| 4,416,654 | 11/1983 | Schoendorfer et al. ............ 604/6 |
| 4,605,503 | 8/1986 | Bilstad et al. ............ 210/651 |
| 4,637,813 | 1/1987 | DeVries ............ 604/6 |
| 4,648,866 | 3/1987 | Malbrancq et al. ............ 604/5 |
| 4,655,742 | 4/1987 | Vantard et al. ............ 604/6 |
| 4,668,399 | 5/1987 | Duggins ............ 210/651 |
| 4,675,117 | 6/1987 | Neumann et al. ............ 210/789 |
| 4,680,025 | 7/1987 | Kruger et al. ............ 604/6 |
| 4,687,580 | 8/1987 | Malbrancq et al. ............ 210/651 |
| 4,713,176 | 12/1987 | Schoendorfer et al. ............ 210/645 |
| 4,776,964 | 10/1988 | Schoendorfer et al. ............ 210/782 |
| 4,790,942 | 12/1988 | Shmidt et al. ............ 210/321.87 |
| 4,808,307 | 2/1989 | Fishel et al. ............ 210/321.87 |
| 4,850,995 | 7/1989 | Tie et al. ............ 604/6 |
| 4,850,998 | 7/1989 | Schoendorfer ............ 604/6 |
| 4,851,126 | 7/1989 | Schoendorfer ............ 210/651 |
| 4,871,462 | 10/1989 | Fischel et al. ............ 210/651 |
| 4,936,980 | 6/1990 | Yoshimichi et al. ............ 210/651 |
| 4,944,883 | 7/1990 | Schoendorfer et al. ............ 210/782 |
| 4,963,253 | 10/1990 | Yen ............ 210/645 |

OTHER PUBLICATIONS

Abstract of DE 3626-498A-A milk filtration system in which concentrate is recycled (1988).

Primary Examiner—Robert A. Dawson
Assistant Examiner—Sun Uk Kim
Attorney, Agent, or Firm—Bradford R. L. Price; Paul C. Flattery; Daniel D. Ryan

[57] ABSTRACT

A processing system separates a cellular rich suspension into a cellular first constituent and cellular-free second constituent. The system includes a separation zone that receives the cellular rich suspension and discharges the first and second constituents. The system coordinates the flow of cellular rich suspension into the separation zone with the flow of the cellular-free second constituent from the separation zone to get a desired nominal separation efficiency. The system also recirculates the cellular first constituent back into the zone. By continuously recirculating the cellular first constituent back into the separation zone, the system is can get and maintain a desired volume of the first constituent, despite the volume of cellular rich suspension that is processed. By continuously recirculating the cellular first constituent back into the separation zone, the system also can provide operating conditions within the separation zone that maximize separation efficiencies but that, without the benefits of recirculation, could otherwise damage or traumatize the cellular first constituent.

33 Claims, 3 Drawing Sheets

SYSTEMS AND METHODS FOR PROCESSING CELLULAR RICH SUSPENSIONS

FIELD OF THE INVENTION

The invention generally relates to fluid processing systems and methods. In a more particular sense, the invention relates to systems and methods for processing suspensions containing fragile cellular material that is subject to trauma when stressed. The invention therefore relates to systems and methods for processing whole blood and concentrations of cellular red blood cell and platelet constituents.

BACKGROUND OF THE INVENTION

With the coming of blood component therapy, most whole blood collected today is separated into its clinically proven components for storage and administration. The clinically proven components of whole blood include red blood cells, used to treat chronic anemia; platelet-poor plasma, from which Clotting Factor VIII-rich cryoprecipitate can be obtained for the treatment of hemophilia; and concentrations of platelets, used to control thrombocytopenic bleeding.

In a typical conventional processing method, whole blood is first separated by centrifugation into red blood cells and platelet-rich plasma. The platelet-rich plasma is then processed into platelet concentrate and platelet-poor plasma by further centrifugation or by a separate filtration step.

Figure 1:
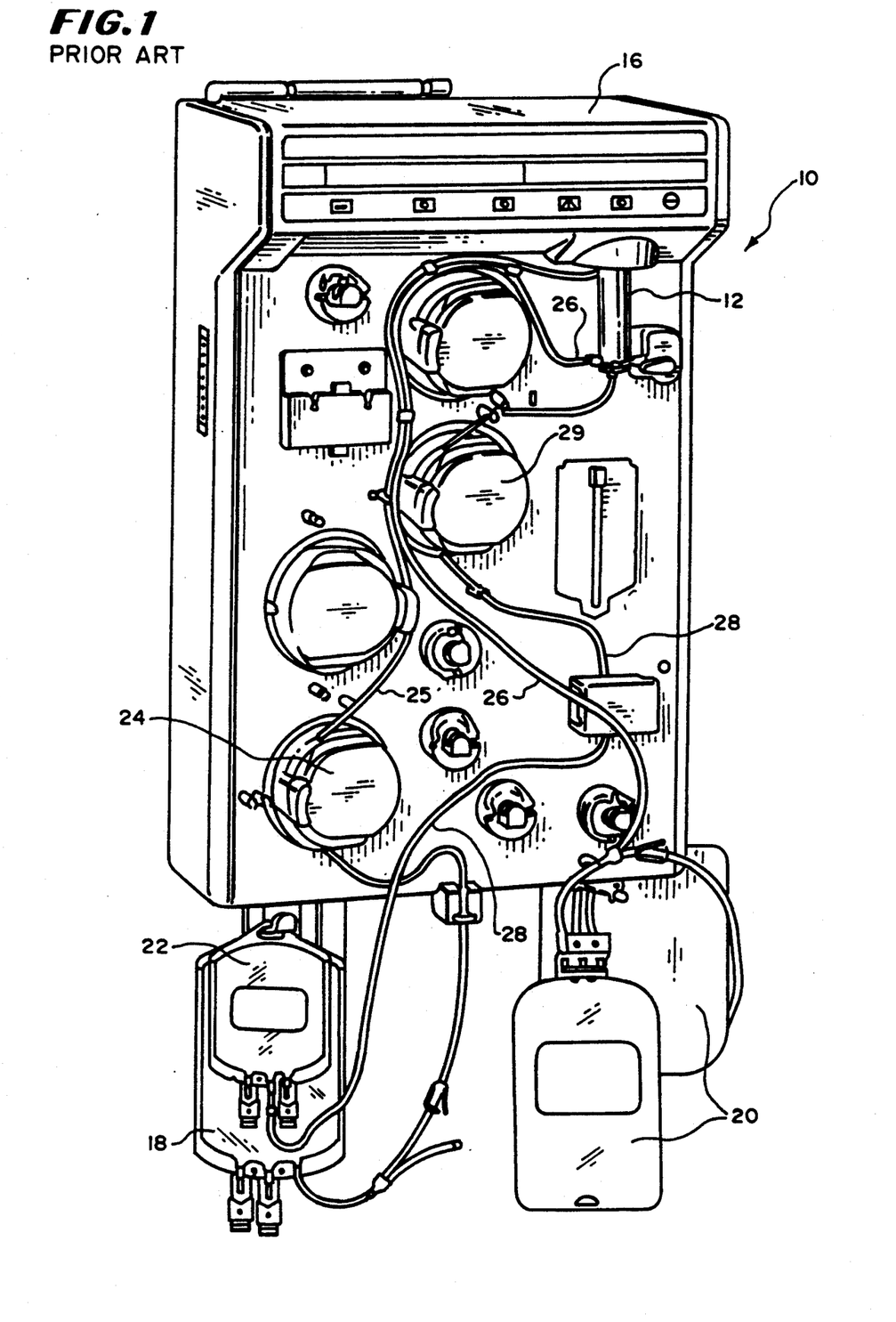
FIG. 1 is a perspective view of a representative prior art processing system for cellular rich suspensions.
Figure 2:
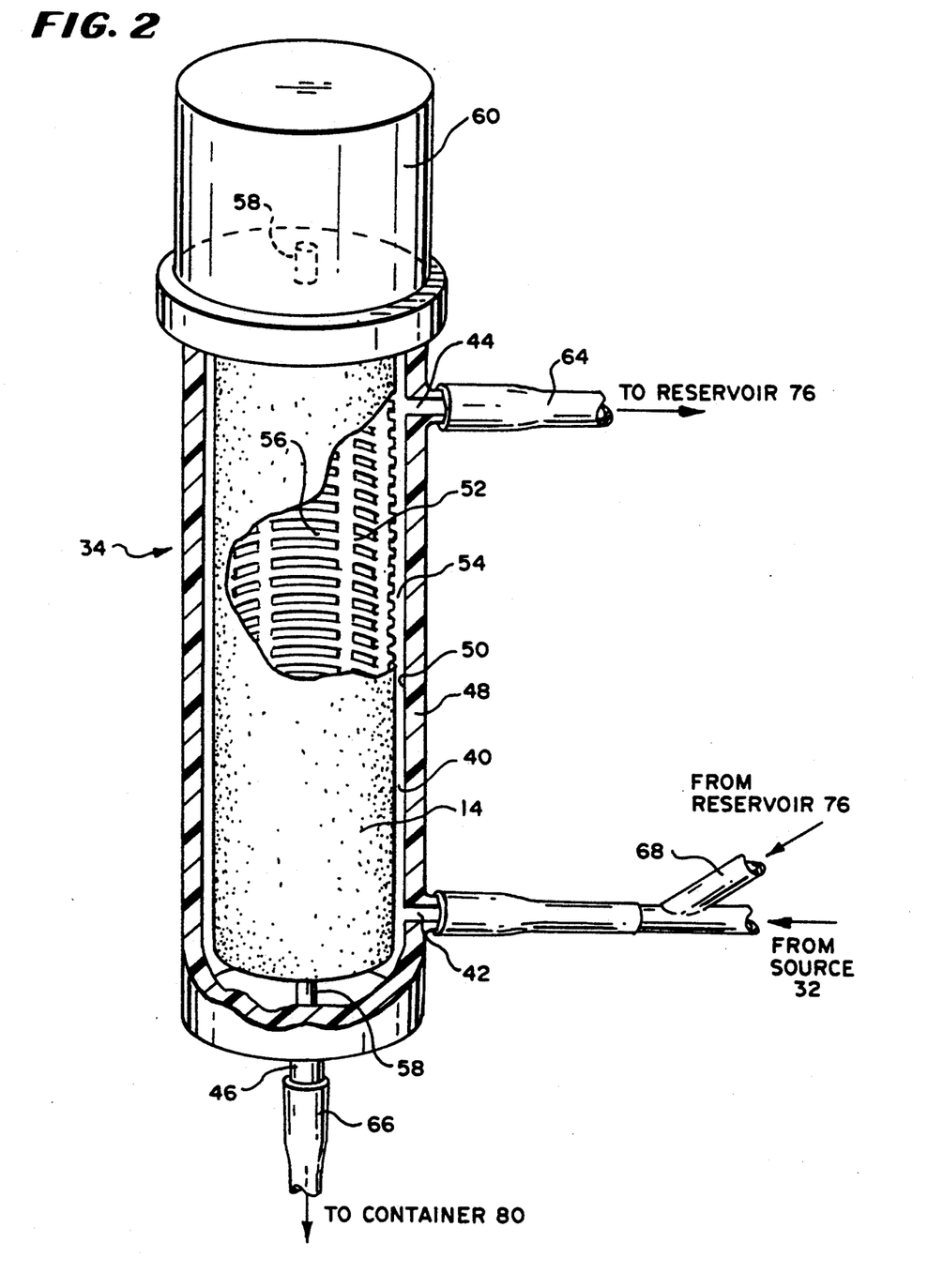
FIG. 2 is a perspective view, with portions broken away and in section, of a conventional rotary membrane separation device that is used in association with the system shown in FIG. 1.

FIG. 1 shows a representative prior art system 10 for processing platelet-rich plasma to obtain platelet concentrate and platelet-poor plasma by filtration. The system 10 includes a membrane separation device 12 of the type shown in copending U.S. patent application Ser. No. 052,171, filed May 5, 1987, and entitled "Blood Fractionation System and Method." The device 12 employs a rotating microporous membrane 14 to separate platelets from platelet-rich plasma. The device 12 also can be used to separate red blood cells from whole blood. The separation device 12 is also shown in FIG. 2 and will be described in greater detail later.

A separation device 12 like that described and claimed in the '171 Application is commercially sold by the Fenwal Division of Baxter Healthcare Corporation under the trademark "Plasmacell-C" ™.

As FIG. 1 shows, the separation device 12 is used in association with a processing apparatus 16. A processing apparatus like that shown in FIG. 1 is sold by the Fenwal Division of Baxter Healthcare Corporation under the trademark "Autopheresis-C" ™.

The system 10 shown in FIG. 1 can process about 600 ml to 700 ml of platelet-rich plasma in about 15 minutes. The platelet-rich plasma to be processed is typically first collected in a container 18 in a preliminary separation step, during which whole blood from a donor is centrifugally separated into red blood cells and platelet-rich plasma. The collected platelet-rich plasma is then pumped from the container 18 into the separation device 12 at a flow rate of about 50 ml/min., while the membrane is rotated at about 1600 RPM's. The platelets are separated from the platelet-rich plasma in a single pass through the separation device 12. Platelet-poor plasma is pumped into a collection container 22 at a flow rate of about 35 ml/min. The platelet concentrate flows into a collection container 20.

As used in the above manner, the separation device 12 operates at a separation efficiency of about 70%. This means that 70% of the total plasma volume contained in the platelet-rich plasma that is delivered to the device 12 is ultimately collected as platelet-poor plasma. The remaining volume (about 200 ml) is the plasma in which the platelet concentrate is suspended.

Thousands of these procedures have been successfully done using the system 10 shown in FIG. 1. Still, there remains a demand for new systems and methods that can process even larger volumes of fragile cellular rich suspension at even higher flow rates. High volume processing of cellular suspensions containing platelets pose even additional challenges, because platelets are among the most fragile and easily traumatized of the cellular constituents of blood.

SUMMARY OF THE INVENTION

The invention provides improved systems and methods for processing large volumes of fluid suspensions rich in cellular material quickly and without damaging the cellular material.

One aspect of the invention provides a system for separating a cellular rich suspension into a first constituent and second constituent. The first constituent comprises a concentration of the cellular material, and the second constituent comprises a fluid essentially free of the cellular material.

In this aspect of the invention, the system includes means for conveying the cellular rich suspension into a separation zone while conveying the second constituent from the separation zone. The system also includes means for conveying the cellular first constituent from the separation zone while recirculating at least a portion of the conveyed first constituent back into the separation zone to join the cellular rich suspension in the separation zone.

In a preferred embodiment, the separation zone includes an inlet, a first outlet for the filtered first constituent, and a second outlet for the filtered second constituent. In this embodiment, the system includes four fluid paths that communicate with the inlet and outlets of the separation zone. The system also includes a control mechanism for coordinating the flow of materials through the various fluid paths.

The first path communicates with a source of the cellular rich suspension and the inlet of the separation zone. The first path includes a first inlet pump for transporting the cellular rich suspension from the source and into the separation zone.

The second path communicates with the first outlet and includes a first outlet pump for transporting the first constituent from the separation zone. The second path also includes a reservoir for collecting a volume of the first constituent conveyed from the separation zone by the first outlet pump.

The third path communicates with the second outlet and includes a second outlet pump for transporting the second constituent from the separation zone.

The fourth path communicates with the reservoir and the inlet of the separating zone. The fourth path includes a second inlet pump for transporting the first constituent collected in the reservoir back into the separation zone.

In a preferred embodiment, one aspect of the control mechanism associated with the system coordinates the operation of the first inlet pump with the second outlet pump. This aspect of the control mechanism maintains a desired relationship between the outlet flow of the cellular free second constituent in the third path relative to the inlet flow of the cellular rich suspension in the first path. In establishing this relationship, the control mechanism imposes a desired nominal separation efficiency for separating cellular free second constituent from the cellular rich suspension within the separation zone.

In a preferred embodiment, another aspect of the control mechanism associated with the system coordinates the operation of the second inlet pump with the first outlet pump. This aspect of the control mechanism maintains another desired relationship between the outlet flow of the cellular first constituent into the reservoir relative to the inlet flow of the cellular first constituent from the reservoir and back into the separation zone. In establishing this relationship, the control mechanism continuously recirculates the cellular first constituent from the reservoir means back into the separation zone.

In a preferred embodiment, the separation occurs within the zone by filtration.

The recirculation of the cellular first constituent back into the separation zone serves several important purposes. By recirculating, the system can first collect and then maintain a desired fixed volume of the first constituent in the reservoir, despite the volume of cellular rich suspension that is processed. By recirculating, the system also can establish operating conditions within the separation zone that maximize separation efficiencies at high flow rates. Without recirculating the cellular first constituent, these same operating conditions could damage or traumatize the cellular first constituent.

Another aspect of the invention provides a method for processing a fluid suspension rich in cellular material. In the method, the cellular rich suspension is conveyed into the separation zone, where it is separated into the first and second constituents, as described in the proceeding paragraphs. According to the method, the first and second constituents are conveyed from the separation zone. The first constituent is recirculated back into the separation zone.

In a preferred embodiment, the method that embodies the features of the invention maintains a desired relationship between the flow of the cellular rich suspension and the flow of the second constituent. This relationship creates a desired high nominal separation efficiency. In a preferred embodiment, the method also maintains a desired relationship between the recirculating flow of the cellular first constituent back into the separation zone. According to the invention, the recirculation can occur with or without altering the volume of the first constituent contained in the reservoir.

In a preferred embodiment of the method, separation occurs by filtration.

The systems and methods that embody the features of the invention allow large volumes of cellular rich suspensions to be efficiently processed at high flow rates in a way not possible with conventional systems and methods. Despite high separation efficiencies and flow rates, the systems and methods that embody the features of the invention cause no discernible damage to fragile cellular materials like platelets.

Other features and advantages of the invention will be pointed out in, or will become apparent from, the drawings, specification and claims that follow.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

Figure 3:
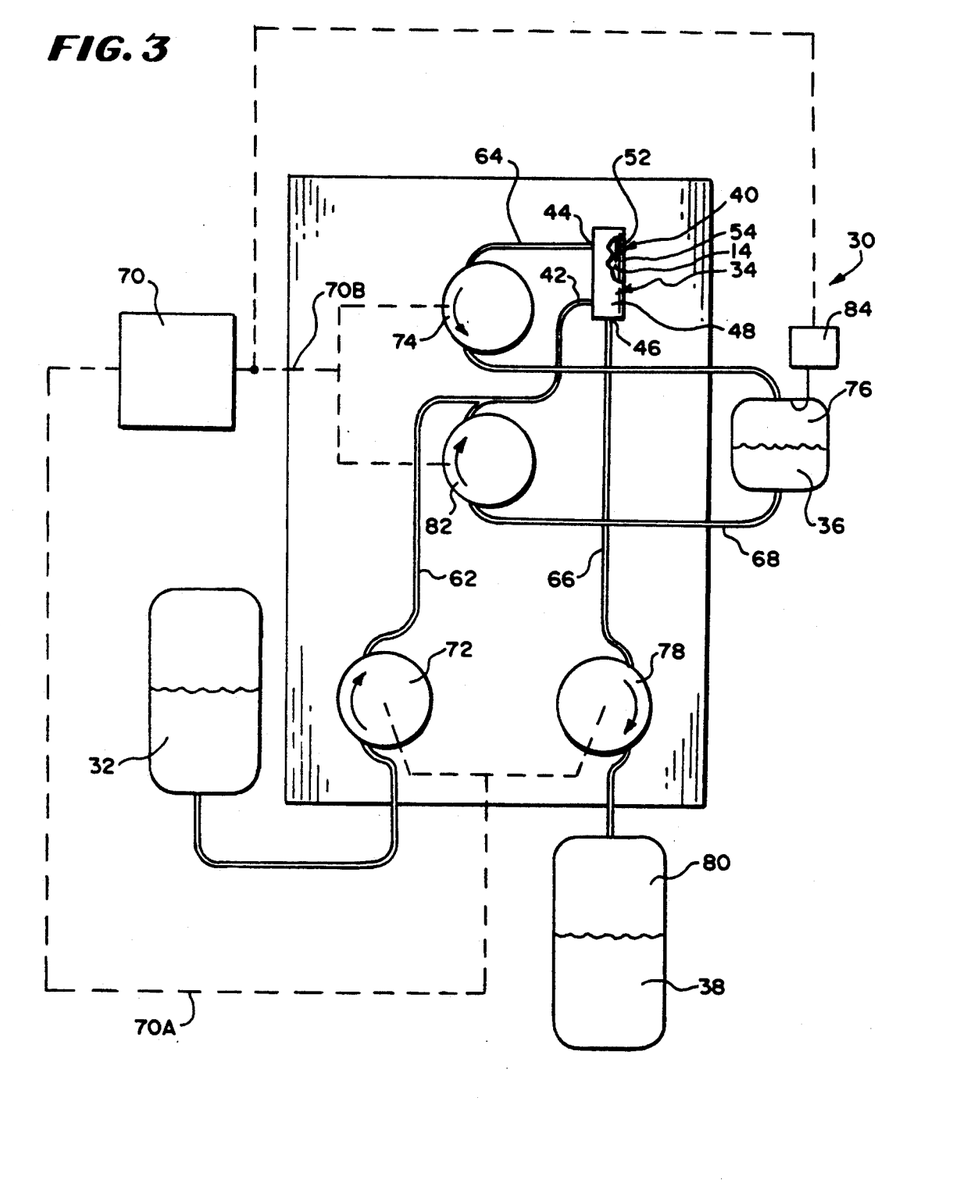
FIG. 3 is a schematic view of a system for processing cellular rich suspensions that embodies the features of the invention.

FIG. 3 shows a system 30 for processing a fluid suspension rich in cellular material according to the invention. The system 30 can process large volumes of cellular rich suspension at relatively high flow rates while maintaining a high separation efficiency. The system 30 is particularly well suited for the rapid processing of large volumes of suspensions containing fragile materials, such as blood and other biological cells. So, the system 30 will be described as being used to process platelet-rich plasma into platelet concentrate and platelet-poor plasma. Yet, the system 30 is applicable for use in other environments.

As FIG. 3 shows, the system 30 includes a source 32 of a cellular rich suspension that is to be processed. In the illustrated embodiment, the source 32 contains a volume of platelet-rich plasma obtained from the whole blood of a human donor.

The system 30 can process the platelet rich plasma as a batch from the source 32. Alternatively, the system 30 can be part of a continuous, on line processing system. In this arrangement, the source 32 could include an upstream processing system (not shown). The upstream processing system receives whole blood from a donor and separates the whole blood into red blood cells and platelet-rich plasma using, for example, centrifugation. The upstream processing system returns the red blood cells to the donor, while conveying the platelet-rich plasma on to the system 30 for further processing according to the invention.

The system 30 includes means 34 for separating the cellular rich suspension into a two constituents 36 and 38. The first constituent 36 comprises a concentration of the cellular material. The second constituent 38 comprises a fluid essentially free of the cellular material. In the illustrated embodiment, the first constituent 36 is platelet concentrate, and the second constituent 38 is platelet-poor or depleted plasma.

As used in this Specification, plasma is "platelet-rich" when it contains platelets in a concentration of about twice that normally found in the whole blood of the donor. Generally, the normal concentration of platelets in a healthy adult is about 200,000 platelets per microliter of whole blood. Therefore, the associated platelet-rich plasma from this donor would contain a platelet concentration of about 400,000 platelets per microliter of plasma.

As used in the Specification, plasma is "platelet-poor" or "platelet depleted" when essentially all the platelets have been removed or when the residual platelets in the plasma do not provide the intended therapeutic effect. Typically, a platelet concentration of about 12,000 platelets per microliter of plasma or less is "platelet-poor" or "platelet-depleted." The medical community generally recognizes that the infusion of platelets in these small concentrations exerts no significant therapeutic effect upon the human body, when compared to the therapeutic effect of infusions of platelets in larger concentrations. The therapeutic value of platelet-poor plasma is due to the plasma and plasma-based components, and not the platelets. Platelet-poor plasma can itself be infused for therapeutic purposes, or it can be used a source plasma for fractionation purposes.

As used in this Specification, platelets are in "concentrated" form when they are present in a concentration that meets or exceeds the prevailing minimum platelet yield requirements prescribed by governing regulations. Typically, a therapeutic unit of concentrated platelets contains about 200 ml of residual plasma. In the United States, Federal Regulations (Title 21 C.F.R. Section 640.24(c)) require the presence of about $5.5 \times 10^{10}$ platelets per therapeutic unit.

As FIG. 3 shows, the separation means 34 includes a zone 40 where the separation process occurs. An inlet 42 brings materials into the zone 40 for separation. The separation means 34 also includes a first outlet 44 for transporting the first constituent 36 from the separation zone 40 and a second outlet 46 for transporting the second constituent 38 from the separation zone 40.

The construction of the separation means 34 can vary. In the illustrated embodiment, the separation means 34 processes the cellular rich suspension using filtration.

The particular separation means 34 used is the membrane filtration device 12 shown in FIG. 2. As previously stated, the device 12 is described and claimed in U.S. patent application Ser. No. 0521,171, filed May 5, 1987, and entitled "Blood Fractionation System and Method." The disclosure in the '171 Application is incorporated in this Specification by reference.

This type of membrane separation device 12 includes a housing 48 having an interior wall 50. The housing 48 carries an interior rotor or spinner 52. A gap 54 extends between the exterior of the rotor 52 and the housing's interior wall 50. The gap 54 constitutes the separation zone 40, as already described.

In the illustrated embodiment, the gap 54 has a width of about 0.020 inch, and a length of about 3.0 inches. The inlet 42 leads into the gap 54.

The rotor 52 carries a microporous membrane 14. The pores of the membrane 14 block the passage of the cellular first constituent 36, while permitting the fluid second constituent 38 to pass through. In the illustrated embodiment, where the cellular first constituent is platelets, the membrane has a pore size of about 0.65 um.

The cellular first constituent 36 exits the separation gap 54 through the previously described first outlet 44. A series of channels 56 extending on the rotor 52 behind the membrane 12 carry the fluid second constituent 38 to the previously described second outlet port 46.

Bearings 58 carry the rotor 52 for rotation within the housing 48. The rotor 52 is magnetically coupled to a driver 60 for rotation at a selected surface velocity. When rotated, the membrane-carrying spinner 52 creates movement of the fluid suspension within the gap 54. This movement (which takes the form of vortices technically known as Taylor Vortices) induces transport of the cellular material away from the membrane 12 while the fluid suspension is transported to the membrane 12. Enhanced separation of the first and second constituents 36 and 38 occurs.

It should be appreciated that, in an alternate embodiment, the interior wall 50 of the housing 48 could carry the membrane 12. Rotation of the spinner 52 (in this embodiment, without the membrane 12) will cause the same vortices to develop and lead to the same enhance separation results. In this arrangement, the interior wall 50 of the housing 48 would include the channels 56 for conveying the second constituent 38 to the second outlet port 46.

Processing of cellular rich suspensions at high flow rates poses difficulties. One difficulty lies in keeping the cellular constituents away from the surface of the membrane to prevent plugging or blocking the pores of the membrane. Another difficulty lies in keeping the cellular constituents safe from damage or trauma.

These difficulties exist despite the particular configuration of the separation means 34. Still, these difficulties will now be discussed in the context of maximizing the high flow processing of cellular rich suspensions using the separation device 12.

One way to increase the rate at which the separation occurs in the device 12, thereby accommodating high flow processing, is to maximize the speed at which the spinner 52 is rotated. Generally speaking, the greater the surface velocity of the membrane 14 is, the better the expected transport of cellular matter away from the membrane 14 can be. This outward transport minimizes plugging of the membrane 14. It also enhances the transport of second constituent 38 across the membrane 14. Still, spinning the rotor 52 at high velocities creates considerable shear stresses within the somewhat narrow separation gap 54. The shear stresses at high speeds of rotation can damage or traumatize cellular material passing within the gap 54. For platelets, shear stresses also cause the platelets to activate and aggregate or "clump" at the membrane surface, plugging the pores of the membrane 14.

Another way to increase the rate at which the separation occurs in the device 12 is to increase the residence time of the cellular material within the separation zone 54. This increases the separation of the membrane 14. Still, as residence time increases, so too does exposure to the separation forces at work within the gap 54. As residence exposure time increases, it becomes more likely that the cellular material will ultimately be damaged or become activated, plugging the membrane 14.

To overcome these impediments to high speed and efficient processing of cellular rich suspension, the system 30 includes first, second, third, and fourth conduit means 62; 64; 66; and 68 associated with the separation means 34. The four conduit means 62; 64; 66; and 68 form fluid paths that convey materials into and out of the separation zone 40 through the respective inlet and outlets 42; 44; and 46. The system 30 also includes control means 70 the coordinates the operation of the four conduit means 62; 64; 66; and 68.

The first conduit means 62 communicates with the inlet 42 of the separation means 34 and the source 32 of the cellular rich suspension. In use, the first conduit means 62 conveys the cellular rich suspension into the separation zone 40. The first conduit means 62 includes a first inlet pump 72 for transporting the cellular rich suspension from the source 32 and into the separation zone 40 at a controlled, preselected flow rate.

The second conduit means 64 communicates with the first outlet 44 for conveying the cellular first constituent 36 from the separation zone 40. The second conduit means 64 includes a first outlet pump 74 for transporting the first constituent 36 from the separation zone 40 at a controlled, preselected flow rate.

The second conduit means 64 empties into an in-line reservoir 76. A volume of the first constituent 36 collects in the reservoir 76 during processing. In the illustrated embodiment, the reservoir 76 that contains the collected volume of first constituent (platelet concentrate) 36 can be separated from the system 30 after processing.

The third conduit means 66 communicates with the second outlet 46 for conveying the second constituent 38. The third conduit means 66 includes a second outlet pump 78 for transporting the second constituent 38 from the separation zone 40 at a controlled, preselected flow rate.

In the illustrated embodiment, the third conduit means 66 also includes one or more containers 80 for collecting the second constituent 38. In the illustrated embodiment, the containers 80 of the collected second constituent (platelet-poor plasma) 38 can be separated from the system 30 after processing. Alternatively, the second constituent 38 can be returned to the donor or undergo additional processing.

The fourth conduit means 68 communicates with the reservoir 76 and the inlet 42 that leads into the separation zone 40. The fourth conduit means 68 includes a second inlet pump 82 for circulating the first constituent 36 collected in the reservoir 76 back into the separation zone 40 at a controlled, preselected flow rate.

By operating the first outlet pump 74 and the second inlet pump 82, the cellular first constituent can be recirculated through the separation zone 40 while the cellular rich suspension is being processed. The recirculation path leads from the first outlet 44, through the reservoir 76, and back to the separation zone 40 through the inlet 42.

The system 30 includes control means 70 for coordinating the operation of the two inlet pumps 72 and 82 and the two outlet pumps 74 and 78. The coordination achieved by the control means 70 allows large volumes of cellular rich suspension to be processed at relatively high flow rates within the separation zone 40, while maintaining high separation efficiencies. The control means 70 also permits large volume and highly efficient processing without damaging or causing trauma to fragile cellular materials traversing the separation zone 40.

To get these results, the control means 70 monitors and controls two aspects of system performance. One aspect (shown diagrammatically in dotted connection lines 70A in FIG. 3) affects the nominal efficiency of separating the second constituent from the cellular rich flow. The other aspect (shown diagrammatically in dotted connection lines 70B in FIG. 3) affects the overall processing efficiency of the system, including the exposure of cellular materials to the forces at work within the separation zone 40.

In monitoring and controlling the first aspect 70A of system performance, the control means 70 coordinates the operation of the first inlet pump 72 and the second outlet pump 78. This aspect 70A of the control means 70 maintains a selected relationship between the flow of the second constituent 38 leaving the separation zone 40 (in the third conduit means 66) relative to the flow of cellular rich suspension entering the separation zone 40 (in the first conduit means 62).

In the illustrated embodiment, this aspect 70A of the control means 70 coordinates delivery of platelet-rich plasma into the separation zone 40 with the removal of platelet-poor plasma from the separation zone 40. The objective of this aspect 70A of the control means 70 is to get a high nominal separation efficiency.

The high nominal separation efficiency reflects the efficiency of removing the second constituent 38 (platelet-poor plasma) from the incoming cellular rich suspension (platelet-rich plasma). The following formula expresses this relationship:

$$E_N = \frac{R_{O2}}{R_{I1}} \qquad \text{EQUATION (1)}$$

where $E_N$ is the nominal separation efficiency;
$R_{O2}$ is the flow rate of the second constituent 38 (platelet-poor plasma) in the third conduit means 66; and
$R_{I1}$ is the flow rate of the cellular rich suspension (platelet-rich plasma) in the first conduit means 62.

In monitoring and controlling the first aspect 70A of system performance, the control means 70 operates to maintain $R_{O2}$ as close to $R_{I1}$ as possible. The control means 70 thereby seeks to obtain a nominal high separation efficiency $E_N$ as close to unity, or 100%, as possible. This high separation efficiency $E_N$ is required to accommodate the time demands of high volume processing.

In monitoring and controlling the second aspect 70B of system performance, the control means 70 coordinates the operation of the second inlet pump 82 with the first outlet pump 74. This aspect 70B of the control means 70 maintains a desired relationship between the flow of the first constituent 36 leaving the separation zone 40 and being collected in the reservoir 76 (via the second conduit means 64), relative to the flow of the first constituent 36 reentering the separation zone 40 from the reservoir 76 (via the fourth conduit means 68).

In the illustrated embodiment, this aspect 70B of the control means 70 supplies a desired volume of platelet concentrate into the reservoir 76 while also recirculating platelet concentrate back into the separation zone 40. This aspect 70B of the control means 70 thereafter maintains the desired volume of platelet concentrate within the reservoir 76, while continuing to recirculate platelet concentrate back into the separation zone 40.

As will be described in greater detail later, this aspect 70B of the control means allows high speed processing to proceed without damaging fragile cellular materials.

This aspect 70B of the control means 70 operates in two phases. In the first phase, the control means 70 maintains the flow rate of the first outlet pump 74 ($R_{O1}$) above the flow rate of the second inlet pump 82 ($R_{I4}$). During this phase of operation, there is a net increase of platelet concentrate volume in the reservoir 76 as platelet concentrate recirculates through the separation zone 40.

This aspect 70B of the control means includes weight sensing means 84 associated with the reservoir 76. By sensing weight, the sensing means 84 indirectly senses the volume of cellular first constituent 36 within the reservoir 76. When the sensing means 84 detects a desired end volume, this aspect 70B of the control means 70 shifts from the first phase to a second phase. During the second phase, the control means 70 maintains the flow rate of the first outlet pump 74 ($R_{O1}$) at generally the same flow rate as the second inlet pump 82 ($R_{I4}$).

During this p of operation, there is no net change in the desired end volume of platelet concentrate collected within the reservoir 76, even as additional volumes of cellular rich suspension are continuously brought into the separation zone 40 and even as the cellular first constituent 36 continuously recirculates through the separation zone 40.

The coordinated flows of cellular rich suspension into the separation zone 40, of the first and second constituents from the separation zone, and the recirculation of the first constituent back through the separation zone 40, contribute to creating the overall performance efficiency for the system. The following formula expresses this overall performance efficiency of the system:

$$E_P = \frac{R_{O2}}{R_{I1} + R_{I4}} \quad \text{EQUATION (2)}$$

where:
$E_P$ is the overall efficiency of system performance;
$R_{O2}$ and $R_{I1}$ are as defined above; and
$R_{I4}$ is the flow rate of the first constituent (platelet concentrate) in the fourth conduit means 68.

As shown above, by recirculating cellular first constituent 36 back through the separation zone 40, the control means 70 provides an overall system performance efficiency $E_P$ that is lower than the nominal separation efficiency $E_N$ (Equation (1)).

In practical effect, the recirculation of the cellular first constituent 36 through the separation zone 40 increases the effective flow rate of materials through the separation zone 40. The cellular material (contained both in the incoming cellular rich suspension and in the recirculated cellular first constituent) therefore ultimately makes repeated, but relatively rapid passes through the separation zone 40. This reduces the residence time exposure of the cellular material to the potentially stressful operating conditions of the separation zone 40 during each pass through the separation zone 40.

In the illustrated embodiment, because the platelet concentrate is continuously and rapidly recirculated through the separation zone 40, the system 30 can provide operating conditions within the separation zone 40 that maximize separation efficiencies without damaging or traumatizing the platelets. Without recirculating the platelet concentrate according to the invention, the same operating conditions could not be maintained within the processing zone 40 without causing damage or trauma to the platelets. This is because, without recirculation, the platelets are exposed to a longer residence time in traversing the separation zone 40.

By recirculation, the invention accumulates an effective total residence time through a series of repeat passes each of short duration through the separation zone 40.

The following examples demonstrate the ability of the system 30 that embodies the features of the invention to process large volumes of cellular rich suspension at relatively high flow rates, while maintaining a high separation efficiency and without damaging fragile cellular components.

EXAMPLE 1

Without Recirculation of the Cellular Constituent

A series of tests were conducted to determine whether a conventional system could process 4200 ml of platelet-rich plasma in one hour to obtain an acceptable platelet concentrate volume of 200 ml.

To obtain a 200 ml volume of platelet concentrate from 4200 ml of platelet-rich plasma, the plasma would have to be removed in the ratio of 21 to 1. That is, for every 21 ml of platelet rich plasma, only 1 ml should be collected with the platelet concentrate. This amounts to a separation efficiency (as computed according to Equation (1) above) of 94%.

A conventional prior art system shown in FIG. 1 was set up. The system included a rotary separation device 12 (as described above and shown in FIG. 2). The separation device 12 was attached to a conventional control apparatus 16 sold by the Fenwal Division of Baxter Healthcare Corporation under the trademark "Autopheresis-C" ®. A volume of platelet-rich plasma was conveyed by a pump 24 into the separation device 12 through the conduit 25. Platelet concentrate was collected in the container 20 through the conduit 26. Platelet-poor plasma was collected in the container 22 through the conduit 28 via the pump 29.

The membrane 14 was rotated at 1800 RPM's. The pump 24 was operated to deliver the platelet-rich plasma into the separation device at a flow rate of 65 ml/min. The pump 29 was operated to conduct platelet-poor plasma from the separation device 12 at a flow rate of 61 ml/min. This provided the desired separation efficiency (as computed according to Equation (1) above) of 94%.

At the outset, the platelet concentrate entering the collection container 20 was observed to have "clumped" due to exposure to the operation conditions within the separation zone 40. The transmembrane pressure of the device 12 also increased dramatically (from 85 mmHg to over 300 mmHg), indicating that the membrane 14 was plugging. Due to the resulting negative high pressure in the plasma outlet conduit 28, the actual efficiency of the plasma pump 29 dropped to 79%. As a result, less plasma was removed in the form of platelet-poor plasma. The fluid volume of platelet concentrate ended up to be three times (3×) greater than desired.

Several of these tests were performed. The same unsatisfactory results were achieved.

From these tests, it became apparent that the rotation of the membrane had to be reduced below 1800 RPM's to prevent damage and activation to the platelets. Still, the 1800 RPM's were already too low, allowing the membrane to plug.

The above example demonstrates that the conventional system cannot be operated at a separation efficiency of 94% and accommodate a high inlet flow rate of 64 ml/min.

EXAMPLE 2

With Recirculation of the Cellular Constituent

A system was set up as shown in FIG. 3.

Platelet-rich plasma was conveyed into the separation zone at a high inlet flow rate of 70 ml/min. Platelet-poor plasma was removed from the separation zone 40 at a rate of 65 ml/min. The first outlet pump 74 was operated to convey platelet concentrate to the reservoir at a rate of 30 ml/min., while the second inlet pump 78 was operated to recirculate platelet concentrate back into the separation zone at a rate of 25 ml/min. This resulted in an increase in the volume of platelet concentrate in the reservoir 76 over time. The membrane was rotated at 3400 RPM's.

In this system the nominal separation efficiency (calculated according to Equation (1) above) was 93%. Still, the overall system performance efficiency (calculated according to Equation (2) above) was 68%. This allowed the membrane to be rotated at 3400 RPM's without damaging or activating the platelets and without plugging of the membrane.

This example demonstrates that the system that embodies the features of the invention can obtain a nominal separation efficiency approaching 100% at high flow rates, without damage to fragile cellular components like platelets.

EXAMPLE 3

With Recirculation of the Cellular Constituent

A system was set up as shown in FIG. 3.

The system was initially primed to convey 174 grams of saline into the reservoir 76. Platelet-rich plasma was then conveyed into the separation zone 40 at a rate that was steadily increased to 43 ml/min over a start-up period of fifteen minutes. During this start-up period, the first outlet pump 74 was operated to convey platelet concentrate to the reservoir at a rate of 25 ml/min, while the second inlet pump was operated to recirculate platelet concentrate back into the separation zone 40 at the same rate of 25 ml/min. The membrane was rotated at a rate that was increased during the fifteen minute start-up period from 1400 RPM's to 1800 RPM's.

During the next fifteen minutes of operation, the flow rate of platelet-rich plasma into the separation zone 40 was steadily increased to 60 to 64 ml/min, while the rotation rate of the membrane was steadily increased up to 2700 RPM's. During this period, the flow rate of the first outlet pump 74 was decreased to 22 to 24 ml/min, while the flow rate of the second inlet pump 78 was maintained at 25 ml/min. During this period, the TMP gradually rose and stabilized at about 57 to 59 mmHg. No platelet clumping or membrane blockage was observed.

At the end of this second fifteen minute period, the reservoir 76 contained a fluid volume of 156 grams.

During the next successive 25 minute period of operation, the flow rate of platelet-rich plasma into the separation zone 40 was steadily decreased to 45 ml/min, while rotation of the membrane was brought to about 2600 RPM's. During this period, the first outlet pump 74 was operated at a flow rate of 27 ml/min, while the flow rate of the second inlet pump 78 continued to be maintained at 25 ml/min. During this period, the TMP gradually decreased to about 52 mmHg. Again, no platelet clumping or membrane blockage was observed.

At the end of this 25 minute period, the reservoir 76 contained a fluid volume of 196 grams.

Therefore, the system was able to reduce the fluid volume of the reservoir 76 over time by operating the first outlet pump 74 at a flow rate less than the second inlet pump 78. The system was also able to increase the fluid volume of the reservoir 76 over a time by operating the first outlet pump 74 at a flow rate more than the second inlet pump 78.

This example demonstrates that the system that embodies the features of the invention can continuously process cellular rich suspension at high flow rates, while being able to selectively control the volume of cellular concentrate collected in the reservoir 76.

EXAMPLE 4

Platelet Viability After Recirculation

The platelet concentrate that was collected during the procedure described in Example 3 underwent viability testing during which both Betathromboglobulin (BTG) levels and Hypotonic Shock Response were measured.

The measured BTG levels ranged from 670 IU/ml to 720 IU/ml. A BTG level of zero (0) is ideal. The typical BTG levels for platelet concentrate collected by conventional membrane separation techniques using the device shown in FIG. 1 range between 600 IU/ml to 1500 IU/ml. The typical BTG levels for platelet concentrate collected by conventional manual centrifugal methods range between 2000 IU/ml to 4000 IU/ml. It can be seen that platelet concentrate collected in according to the invention have BTG levels that are comparable to the BTG levels of conventional membrane separation techniques, and better than the BTG levels of conventional manual centrifugation techniques.

The Hypotonic Shock Response measured was between 54% and 68%. A Hypotonic Shock Response of 100% is ideal. The Typical Hypotonic Shock Response for platelet concentrate collected by conventional membrane separation techniques using the device shown in FIG. 1 is about 76% (plus or minus 10%). The typical Hypotonic Shock Response for platelet concentrate collected by conventional manual centrifugal methods is about 67% (plus or minus 8%). It can be seen that platelet concentrate collected in according to the invention display a Hypotonic Shock Response that is comparable to the Hypotonic Shock Response of conventional separation techniques.

This example demonstrates that the system that embodies the features of the invention can continuously process cellular rich suspension at high flow rates without adversely affecting the viability of the platelets, when compared to conventional techniques now in use.

The features and advantages of the invention are set forth in the following claims.

I claim:

1. A system for processing a fluid suspension rich in cellular matter comprising means for defining a separation zone, means for conveying the cellular rich suspension into the separation zone for separation into a first constituent comprising a concentration of the cellular matter and a second constituent essentially depleted of the cellular matter, means for conveying the second constituent from the separation zone, means for conveying the cellular first constituent from the separation zone including means for recirculating at least a portion of the conveyed cellular first constituent back into the separation zone free of added replacement fluid while the cellular rich suspension is also conveyed into the separation zone, and control means for maintaining a desired relationship between the flow of the cellular rich suspension and the flow of the second constituent to obtain a nominal separation efficiency $E_N$ equal to about unity, where $$E_N = \frac{R_{O2}}{R_{I1}}$$

wherein
$E_N$ is the nominal separation efficiency;
$R_{O2}$ is the flow rate of the second constituent; and
$R_{I1}$ is the flow rate of the cellular rich suspension, and for maintaining a desired recirculation flow of the cellular first constituent back into the separation zone to create an overall system performance $E_P$ that is lower than $E_N$, where $$E_P = \frac{R_{O2}}{R_{I1} + R_{I4}}$$

where:
$E_P$ is the overall efficiency of system performance;
$R_{O2}$ and $R_{I1}$ are as defined above; and
$R_{I4}$ is the recirculation flow rate of the cellular first constituent.

2. A system according to claim 1
wherein the means for conveying the cellular first constituent includes a reservoir, and
wherein the control means further operates in a first phase for maintaining a first desired relationship between the flow of the cellular first constituent from the separation zone into the reservoir and the flow of the cellular first constituent from the reservoir for recirculation back into the separation zone to collect a desired volume of the cellular first constituent in the reservoir while recirculation occurs and in the second phase for thereafter maintaining a second desired relationship between the flow of the cellular first constituent from the separation zone into the reservoir and the flow of the cellular first constituent from the reservoir to maintain the volume while recirculation occurs.

3. A system according to claim 1 or 2 wherein the separation zone includes a filtration membrane.

4. A system according to claim 1 or 2 wherein the separation zone includes a housing having an interior wall, a rotor carried within the housing and having an exterior wall spaced from the housing's interior wall to form a gap which communicates with the inlet, membrane means on either the housing's interior surface or the rotor's exterior surface, and means for rotating the rotor within the housing while the membrane means separates the suspension conveyed into the gap.

5. A system for processing a fluid suspension rich in cellular material comprising
means defining a separation zone for separating the cellular rich suspension into a cellular first constituent comprising a concentration of the cellular material and a second constituent comprising a fluid essentially depleted of the cellular material, the separation zone including an inlet, a first outlet for the cellular first constituent, and a second outlet for the second constituent,
first means communicating with the inlet of the separation zone and a source of the cellular rich suspension and including first inlet pumping means for transporting the cellular rich suspension from the source and into the separation zone,
second means for communicating with the first outlet and including first outlet pumping means for transporting the cellular first constituent from the separation zone, the second means including reservoir means for collecting a volume of the cellular first constituent transported by the first outlet pumping means,
third means communicating with the second outlet and including second outlet pumping means for transporting the second constituent from the separation zone,
fourth means communicating with the reservoir means and the inlet of the separation zone and including second inlet pumping means for transporting the cellular first constituent from the reservoir means and into the separation zone; and
control means for operating the first inlet pumping means and the second outlet pumping means for continuously separating and discharging the second constituent from the separation zone, while simultaneously operating the second inlet pumping means and first outlet pumping means for continuously recirculating at least a portion of the cellular first constituent from the reservoir means into the separation zone.

6. A system according to claim 5
wherein the separation zone includes membrane means for filtering the cellular first constituent from the cellular rich suspension.

7. A system according to claim 5
wherein the separation zone includes a housing having an interior wall, a rotor carried within the housing and having an exterior wall spaced from the housing's interior wall to form a gap which communicates with the inlet, membrane means on either the housing's interior surface or the rotor's exterior surface, and means for rotating the rotor within the housing while the membrane means separates the suspension conveyed into the gap into the first and second constituents.

8. A system according to claim 5
wherein the control means operates the second outlet pumping means at a flow rate generally equal to the flow rate of the first inlet pumping means.

9. A system according to claim 5 or 8
and further including sensor means for sensing the volume of the cellular first constituent in the reservoir means, and
wherein the control means initially operates the first outlet pumping means at a flow rate greater than the flow rate of second inlet pumping means until the sensor means detects a desired volume of the cellular first constituent in the reservoir means and then operates the first outlet pumping means at a flow rate generally equal to the flow rate of the second inlet pumping means to maintain the desired volume within the reservoir means while recirculating the cellular first constituent.

10. A system for processing a platelet-rich suspension comprising
a source of platelet-rich plasma,
means for defining a separation zone,
means for conveying the platelet-rich suspension from the source into the separation zone for separation into a concentration of platelets and a second platelet-poor constituent,
means for conveying the second constituent from the separation zone including means for recirculating at least a portion of the conveyed concentration of platelets back into the separation zone without added replacement fluid while the platelet rich suspension is also conveyed from the source into the separation zone.

11. A system according to claim 10 wherein the means for conveying the concentration of platelets includes reservoir means for collecting a volume of the platelet concentration as recirculation occurs.

12. A system according to claim 10 or 11 wherein the means for conveying the platelet-rich suspension, the concentration of platelets, and the second constituent includes means for maintaining the flow of the platelet-rich suspension and the flow of the second constituent at generally the same rate while recirculating the platelet concentration back into the separation zone.

13. A system according to claim 10 or 11 wherein the separation zone includes a filtration membrane.

14. A system according to claim 10 or 11 wherein the separation zone includes a housing having an interior wall, a rotor carried within the housing and having an exterior wall spaced from the housing's interior wall to form a gap which communicates with the inlet, membrane means on either the housing's interior surface or the rotor's exterior surface, and means for rotating the rotor within the housing while the membrane means separates the suspension conveyed into the gap.

15. A system for processing platelet rich plasma into platelet-poor plasma and a concentration of platelets, the system comprising
a source of platelet-rich plasma,
means defining a separation zone for separating plasma from the platelet-rich plasma to form a concentration of platelets, the separation zone including an inlet, a first outlet for the platelet concentrate, and a second outlet for the separated plasma,
first means communicating with the inlet of the separation zone and the source for conveying the platelet-rich plasma and including first inlet pumping for transporting the platelet-rich plasma from the source and into the separation zone,
second means communicating with the first outlet for conveying the platelet concentrate and including first outlet pumping means for transporting the platelet concentrate from the separation zone, the second means including reservoir means for collecting a volume of the platelet concentrate transported by the first outlet pumping means,
third means communicating with the second outlet for conveying the separated plasma and including second outlet pumping means for transporting the separated plasma from the separation zone,
fourth means communicating with the reservoir means and the inlet of the separation zone for conveying platelet concentrate and including second inlet pumping means for transporting the platelet concentrate from the reservoir means and into the separation zone, and
control means for operating the first inlet pumping means and the second outlet pumping means for continuously discharging the separated plasma from the separation device, while simultaneously operating the second inlet pumping means and first outlet pumping means for continuously recirculating the platelet concentrate from the reservoir means into the separation device.

16. A system according to claim 15 wherein the separation zone includes membrane means for filtering platelets from the platelet-rich plasma.

17. A system according to claim 15 wherein the separation zone includes a housing having an interior wall, a rotor carried within the housing and having an exterior wall spaced from the housing's interior wall to form a gap which communicates with the inlet, membrane means on either the housing's interior surface or the rotor's exterior surface, and means for rotating the rotor within the housing while the membrane means separates the suspension conveyed into the gap into plasma and platelet concentrate.

18. A system according to claim 15 wherein the source includes a centrifuge for first separating whole blood into red blood cells and platelet-rich plasma.

19. A system according to claim 15 wherein the control means operates the second outlet pumping means at a flow rate generally equal to the flow rate of the first inlet pumping means.

20. A system according to claim 19 wherein the flow rate of the second outlet pumping means is not less than 5 ml/min of the flow rate of the first inlet pumping means.

21. A system according to claim 19 or 20 wherein the control means initially operates the first outlet pumping means at a flow rate greater than the flow rate of second outlet pump until a desired volume of platelet concentrate is collected in the reservoir means and then operates the first outlet pumping means at a flow rate generally equal to the flow rate of the second inlet pumping means to maintain the desired volume within the reservoir means while recirculating the platelet concentrate.

22. A method for processing a fluid suspension rich in cellular material comprising the steps of
conveying the cellular rich suspension into a separation zone for separation into a cellular first constituent that comprises a concentration of the cellular material and a second constituent that comprises a fluid essentially depleted of the cellular material,
conveying the second constituent from the separation zone,
conveying the cellular first constituent from the separation zone while recirculating at least a portion of the conveyed first constituent back into the separation zone free of added replacement fluids while the cellular rich suspension is also conveyed into the separation zone, and
maintaining a desired relationship between the flow of the cellular rich suspension and the flow of the second constituent to obtain a nominal separation efficiency $E_N$ equal to about unity, where $$E_N = \frac{R_{O2}}{R_{I1}}$$

wherein
$E_N$ is the nominal separation efficiency;
$R_{O2}$ is the flow rate of the second constituent; and
$R_{I1}$ is the flow rate of the cellular rich suspension, while maintaining a desired recirculation flow of the cellular first constituent back into the separation zone to create an overall system performance $E_P$ that is lower than $E_N$, where $$E_P = \frac{R_{O2}}{R_{I1} + R_{I4}}$$

where:
$E_P$ is the overall efficiency of system performance;
$R_{O2}$ and $R_{I1}$ are as defined above; and
$R_{I4}$ is the recirculation flow rate of the cellular first constituent.

23. A method according to claim 22 wherein the step of conveying the cellular first constituent includes the step of collecting and maintaining a volume of the first constituent in a reservoir as recirculation occurs.

24. A method for harvesting platelet concentrate and platelet-poor plasma from platelet-rich plasma comprising the steps of
conveying the platelet-rich plasma from a source into a separation zone for separation into a platelet concentrate and platelet-poor plasma,
conveying the platelet-poor plasma from the separation zone, and
conveying the platelet concentrate from the separation zone while recirculating at least a portion of the conveyed platelet concentrate back into the separation zone without added replacement fluid while the platelet-rich plasma is also conveyed from the source into the separation zone.

25. A method according to claim 24 wherein the step of conveying the platelet concentrate includes the step of collecting a volume of the platelet concentrate in a reservoir as recirculation occurs.

26. A system for processing a fluid suspension rich in cellular matter comprising
means for defining a separation zone,
means for conveying the cellular rich suspension into the separation zone for separation into a first constituent comprising a concentration of the cellular matter and a second constituent essentially depleted of the cellular matter,
means for conveying the second constituent from the separation zone,
means for conveying the cellular first constituent from the separation zone including a reservoir for collecting the cellular first constituent and means for recirculating at least a portion of the conveyed cellular first constituent collected in the reservoir back into the separation zone while the cellular rich suspension is also conveyed into the separation zone, and
control means for maintaining a desired relationship between the flow of the cellular rich suspension and the flow of the second constituent to obtain a nominal separation efficiency $E_N$ equal to about unity, where $$E_N = \frac{R_{O2}}{R_{I1}}$$

wherein
$E_N$ is the nominal separation efficiency;
$R_{O2}$ is the flow rate of the second constituent; and
$R_{I1}$ is the flow rate of the cellular rich suspension, and for recirculating the cellular first constituent in the reservoir back into the separation zone to create an overall system performance $E_P$ that is lower than $E_N$, where $$E_P = \frac{R_{O2}}{R_{I1} + R_{I4}}$$

where
$E_P$ is the overall efficiency of system performance;
$R_{O2}$ and $R_{I1}$ are as defined above; and
$R_{I4}$ is the recirculation flow rate of the cellular first constituent,
by operating in a first phase for collecting a desired volume of the cellular first constituent in the reservoir while recirculation occurs and in a second phase for thereafter maintaining the volume while recirculation occurs.

27. A system for processing a platelet-rich suspension comprising
a source of platelet-rich plasma,
means for defining a separation zone,
means for conveying the platelet-rich suspension from the source into the separation zone for separation into a concentration of platelets and a second platelet-poor constituent,
means for conveying the second constituent from the separation zone,
means for conveying the concentration of platelets from the separation zone while recirculating at least a portion of the conveyed concentration of platelets back into the separation zone while the platelet rich suspension is also conveyed from the source into the separation zone, and
the means for conveying the platelet-rich suspension, the concentration of platelets, and the second constituent including means for maintaining the flow of the platelet-rich suspension and the flow of the second constituent at generally the same rate while recirculating the platelet concentration back into the separation zone.

28. A system according to claim 27 wherein the means for conveying the concentration of platelets includes reservoir means for collecting a volume of the platelet concentration as recirculation occurs.

29. A system according to claim 28 wherein the means for conveying the concentration of platelets includes means for maintaining a desired volume of platelet concentration in the reservoir means as recirculation occurs.

30. A method for processing a fluid suspension rich in cellular material comprising the steps of
conveying the cellular rich suspension into a separation zone for separation into a cellular first constituent that comprises a concentration of the cellular material and a second constituent that comprises a fluid essentially depleted of the cellular material,
conveying the second constituent from the separation zone,
conveying the cellular first constituent from the separation zone while recirculating at least a portion of the conveyed first constituent back into the separation zone while the cellular rich suspension is also conveyed into the separation zone, and maintaining a desired relationship between the flow of the cellular rich suspension and the flow of the second constituent to obtain a nominal separation efficiency $E_N$ equal to about unity, where $$E_N = \frac{R_{O2}}{R_{I1}}$$

wherein $E_N$ is the nominal separation efficiency;

$R_{O2}$ is the flow rate of the second constituent; and $R_{I1}$ is the flow rate of the cellular rich suspension, while collecting and maintaining a volume of the first constituent in a reservoir while recirculating at least a portion of the cellular first constituent from the reservoir back into the separation zone to create an overall system performance $E_P$ that is lower than $E_N$, where $$E_P = \frac{R_{O2}}{R_{I1} + R_{I4}}$$

where:

$E_P$ is the overall efficiency of system performance;

$R_{O2}$ and $R_{I1}$ are as defined above; and $R_{I4}$ is the recirculation flow rate of the cellular first constituent.

31. A method for harvesting platelet concentrate and platelet-poor plasma from platelet-rich plasma comprising the steps of conveying the platelet-rich plasma from a source into a separation zone for separation into a platelet concentrate and platelet-poor plasma, conveying the platelet-poor plasma from the separation zone at generally the same flow rate as platelet-rich plasma is conveyed into the separation zone, and conveying the platelet concentrate from the separation zone while recirculating at least a portion of the conveyed platelet concentrate back into the separation zone while the platelet-rich plasma is also conveyed from the source into the separation zone.

32. A method according to claim 31 wherein the step of conveying the concentration of platelets from the separation zone includes collecting a volume of the platelet concentration in a reservoir as recirculation occurs.

33. A method according to claim 32 wherein the step of conveying the concentration of platelets includes maintaining a desired volume of platelet concentration in the reservoir as recirculation occurs.

* * * * *

UNITED STATES PATENT AND TRADEMARK OFFICE
CERTIFICATE OF CORRECTION

PATENT NO.  : 5,234,608
DATED       : August 10, 1993
INVENTOR(S) : Daniel H. Duff It is certified that error appears in the above-identified patent and that said Letters Patent is hereby corrected as shown below:

In claim 10, at column 14, line 66, between "zone" and "including", insert: -- , and means for conveying the concentration of platelets from the separation zone --.

Signed and Sealed this

Eighth Day of March, 1994

*Attest:*

BRUCE LEHMAN

*Attesting Officer*            *Commissioner of Patents and Trademarks*